United States Patent [19]
Sprotte et al.

[11] Patent Number: 5,871,731
[45] Date of Patent: Feb. 16, 1999

[54] ORAL ADMINISTRATION OF IMMUNOGLOBULIN PREPARATIONS FOR TREATMENT OF CHRONIC PAIN SYNDROME

[76] Inventors: Günter Sprotte, Oberer Bux 7, Randersacker, Germany, D-97236; Helge Karch, Nikolausweg 10, Höchberg, Germany, D-92704; Reinhard Lissner, Haus 18, Gönz-Weilbach, Germany, D-63937; Wolfgang Möller, Stauffenberg Str. 32, Oberursel, Germany, D-61440

[21] Appl. No.: 763,582

[22] Filed: Dec. 10, 1996

[30] Foreign Application Priority Data

Dec. 22, 1995 [DE] Germany ........................ 195 48 221.2

[51] Int. Cl.$^6$ ........................ A61K 39/395; A61K 39/38; A61K 38/00; C07K 16/00
[52] U.S. Cl. ..................................... 424/130.1; 424/135.1; 424/184.1; 530/387.1; 530/388.1; 530/833; 514/2; 514/21
[58] Field of Search .............................. 424/130.1, 135.1, 424/184.1; 530/387.1, 388.1, 833; 514/2, 21

[56] References Cited

U.S. PATENT DOCUMENTS

| | | |
|---|---|---|
| Re. 33,565 | 4/1991 | Stolle et al. . |
| 4,585,651 | 4/1986 | Beck et al. . |
| 4,732,757 | 3/1988 | Stolle et al. . |
| 4,756,907 | 7/1988 | Beck et al. . |
| 4,843,065 | 6/1989 | Collins et al. . |
| 5,066,491 | 11/1991 | Stott et al. . |
| 5,106,618 | 4/1992 | Beck et al. . |
| 5,242,691 | 9/1993 | Beck . |
| 5,352,462 | 10/1994 | Beck . |
| 5,420,253 | 5/1995 | Emery et al. . |
| 5,531,988 | 7/1996 | Paul . |
| 5,531,989 | 7/1996 | Paul . |
| 5,558,993 | 9/1996 | Champion et al. . |
| 5,583,201 | 12/1996 | Cameron et al. . |

FOREIGN PATENT DOCUMENTS

| | | |
|---|---|---|
| 0 225 254 A2 | 6/1987 | European Pat. Off. . |
| 0 338 229 A1 | 10/1989 | European Pat. Off. . |
| 0 338 229 B1 | 10/1989 | European Pat. Off. . |
| 0 469 359 A2 | 2/1991 | European Pat. Off. . |
| WO 96/25155 | 8/1996 | WIPO . |

OTHER PUBLICATIONS

Gantz et al. Drugs 38(6):855–862 1989.
Goldenberg Curr. Opin. Rheumatol. 3:247–258 1991.
Tuncer et al, Clinical Rheumatol. 16(No. 1):9–12 1997.
Henriksson, J. Musculoskeletal Pain, 1/3–4:3–16 (1993).
Kyle et al Am. J. Med, Sci. 303(1):28–34 1992.
Caro et al, J. Rheumahol: 13(6):1086–1092 1986.
Dinerman et al, J. Rheumatol, 13(2):368–373 1986.
Dinerman et al, Annals Internal Medicine 117:281–285 1992.
Eneström et al Scand. J. Rheumatol 26:308–313 1997.
Peterson et al Am. J. Medicine 89:554–560 1990.
Straus et al, Am. J. Med. 89:551–53 1990.
Lloyd et al Am. J. Med. 89:561–568 1990.
Medline 93142956: Abstract of *"Therapy of Post–herpetic Neuralgia"*, Hügler et al, Anaesthesist, Bd. 41, Nr. 12, Dec. 1992.
Medline 88031840: Abstract of *"Double–blind Study of Antitissue Immunoglobulin Injections Versus Placebo in the Treatment of Acute Lumbar Pain with Muscular Spasms"*, Ginsberg et al, International Journal of Clinical Pharmacology, 1987.
*"Therapy of Post–herpetic Neuralgia"*, Hügler et al, Anaesthesist, Bd. 41, Nr. 12 Dec. 1992.
*"Antibodies form Colostrum in Oral Immunotherapy"*, Stephan et al, Journal of Clinical Chemistry and Clinical Biochemistry, Bd. 28, Nr. 1, 1990.
"Musculoskeletal manifestations of Lyme Disease", Steere et al, The American Journal of Medicine, Bd. 98, Nr. 4A, 1995.
Karch et al, J. Clin. Microbiol. 32(9):2312–2314 1994.
Autenrieth et al, Antimicrob. Agents & Chemotherap. 39(9):1965–1969 1995.
Steere. New Eng. J. Med., 321(9):586–96 1989.
Sevier et al, Clin. Chem., 27/11:1797–1806 1981.
Paul (ed). In: Fundamental Immunology 3$^{rd}$ Edition. pp. 1033–1097. Raven Press Ltd. N. Y. 1993.

*Primary Examiner*—Nita Minnifield
*Attorney, Agent, or Firm*—Sprung Kramer Schaefer & Briscoe

[57] ABSTRACT

The invention concerns the oral administration of immunoglobulins from plasma, colostral milk, milk, eggs or cell cultures for the therapy and prophylaxis of heavy therapy-refractory pain conditions in patients without typical pathological anatomical correlates.

10 Claims, No Drawings

ORAL ADMINISTRATION OF IMMUNOGLOBULIN PREPARATIONS FOR TREATMENT OF CHRONIC PAIN SYNDROME

Pain is a frequent accompanying symptom of many banal but also of serious underlying illnesses. The pain may have a meaningful function if it indicates a damage and serves as warning signal for an illness in an early phase, so an early, specific intervention is possible to cure the cause of the pain. The remedy of the cause of the pain often is not possible e.g. in arthritis. If the cause is known, the pain often can be soothed by physical measures or by analgetically effective pharmaceuticals.

An important problem is chronic pain, often suffered from over many years and decades, which cannot be correlated to an acute or chronic disease and therefore is without any anatomical correlation. Often the patients develop great emotional problems which can lead to serious depressions and attempted suicides if the severe pain can not or can only insufficiently be controlled even with the strongest analgetics. From their view, the patients have no prospect because the factors causing pain are mostly unknown. The patients are treated on a long-term basis with opiates or opioids, if they are responding to these drugs. Psychopharmacological drugs and accompanying psychotherapy at best prevent the social insulation of the patients. The pharmacotherapy with anesthetics and psychopharmacological drugs can cause with considerable side effects e.g. reduction of the power of concentration (work, traffic, reading, writing), obstipation, nausea and so on. Beyond this the possible production of physical and emotional dependence and other unwanted side effects with the application of the opioids e.g. miosis, breath depression, blood pressure drop creates problems.

In Germany there approx. 4 000 000 patients estimated to have serious long lasting pain, of which at least 500 000 are regarded as problem cases, because their pain is rated as therapy resistant by the doctor. In other countries, e.g. the USA the conditions are similar in relation to the total population.

The long lasting pain is often occurs particularly in joints, in muscles and connective tissue (e.g. fibromyalgy) and in the back. Chronic pain causes e.g. in the USA a loss of more than 250 million working days per year.

Usually complaints are called chronic pain when they last longer than half a year. In the course of time, chronic pain can come completely to the fore and form a independent clinical syndrome.

Today most of the clinical phenomena of chronic pain syndrome are explained as a permanent excitation of spinal convergence neurons. The permanent excitation is mainly provocable with visceral nociceptive stimuli e.g. via nociceptors in the gut.

Often the patients with chronic pain have pathologically changed parameters of humoral and cellular immunity. Frequently antineuronal antibodies can be detected. In first therapeutic trials some of the patients showed a certain remission of symptoms after the application of intravenous immunoglobulin preparations. In part the patients were responding to analgetics like opioids only when they were administered concomitantly with i.v. immunoglobulins. A long lasting freedom of pain was not achievable with the administration of intravenous immunoglobulins.

The sera of 258 patients with chronic pain syndrome was analysed with the immunoblot technique on antibody activities against different humanpathogenic bacteria. In more than 80% of the patients antibodies against one or several species of the group of *Campylobacter jejuni, Helicobacter pylori,* Human pathogenic *Yersinia enterocolitica* resp. pseudotuberculosis and *Borrelia burgdorferi* sensu lato were detectable (table 1).

TABLE 1

| Serology of patients with chronic pain | | |
|---|---|---|
| Antibodies against | Incidence in chronic pain patients | Incidence in a comparable healthy collective |
| *Campylobacter jejuni* | 30% | <4% |
| *Yersinia sp.* | 20% | <4% |
| *Borrelia burgdorferi sensulato* | 39% | <3% |
| Negative | 19% | >90% |

In spite of the positive antibody findings in the serum the pain patients did not show more of the expected gastric symptoms than healthy people, that means there was no striking accumulation of diarrhea or other symptoms of an acute or chronic gastrointestinal infection. In the stomach and in the intestine of most of the patients no bacteria of the species *Campylobacter jejuni, Helicobacter pylori,* Yersinien or Borrellia were detectable. Even if there were bacteria, e.g. *Helicobacter pylori,* detectable in patients with positive evidence of antibodies in the serum and in most of these cases the eradication of the bacteria by antibiotics was successful, this was followed only in a few cases by a remission of the pain symptoms.

Therefore, it is clear that patients suffering from pain do not have a simple gastrointestinal infection caused by pathogenic bacteria. In fact severe pain in such acute or chronic infections can occur frequently. But this pain is localized in the abdomen and can be clearly assigned to an irritation of the muscous membranes of gastrointestinal tissue due to the effects of e.g. gastric acid or to disorders of motility and colics there.

In chronic pain syndrome however it is not possible to assign the pain locally. Even after a short time of relief following the administration of antibiotics or intravenous immunoglobulins pain attacks continued in undiminished strength. Often the only successful therapy was due to the responsiveness of the patients to opioids to attain a certain relief of pain. At the same time the side effects of opioids occured as described before.

Therefore, object of the invention was to find a therapeutical or prophylactical regimen, providing permanent freedom of pain to patients with chronic pain syndrome whereby side effects of known, analgetics could be avoided.

This object was attained according to the invention by administering to such patients an immunoglobulin preparation orally.

It has been surprisingly discovered that the oral administration of immunoglobulins to patients with chronic pain without typical pathological and anatomical correlates can clearly reduce the pain so that a treatment with the strongest analgetics like e.g. opioids is no longer necessary or is necessary only in reduced dosage neccessary. With regard to the weak effectiveness of intravenously administered immunoglobulins this effect was not expectable.

The immunoglobulins administered according to the invention can be prepared by known techniques from plasma, for example from human blood, from eggs, from milk or from colostral milk or as monoclonal antibodies, belonging to the IgG, IgM and/or IgA-class. As the production of the immunoglobulins from plasma is relativly complicated and therefore very expensive, the immunoglobulins are preferably isolated from milk and most preferably from colostral milk, that means the milk obtained within the first 5 days after the delivery of the calf. Colostral milk has a high content of immunoglobulins, which can be up to more than 50% of the total protein content.

The immunoglobulins, especially those from milk or colostral milk can come from humans or from animals. Preferably the milk, especially the colostral milk is taken from cows, because it is produced in abundant amounts and in particular the colostral milk today is mostly discarded. Especially prefered are immunoglobulins, especially from milk or colostral milk, from non immunized mammals, like e.g. cows, as these already contain high amounts of antibodies against bacterial antigens.

Especially prefered are products with antibody activity against human pathogenic *Yersinia enterocolitica* or *Yersinia pseudotuberculosis, Campylobacter jejunii* and *Borrelia burgdorferi* sensu lato.

Especially prefered is the antibody preparation having the following titers related to an immunoglobulin solution with a content of 5 g/100 ml immunoglobulin: In an immunoblot according to I. Autenrieth et al. (Antimicrobial Agents and Chemotherapy, 39, 1965–1969, 1995) or J. Heesemann et al. (Infection and Immunity, 54, 561–567, 1986) the antibody titer against *Campylobacter jejuni* should be $\geq 1:3200$ and/ the antibody titer against *Yersinia enterocolitica* should be $\geq 1:3200$. In an immunoblot according to H.-I. Huppertz et al. (Eur. J. Pediatr. 153, 898–902, 1994) the antibody titer against Borrelia should be $\geq 1:200$.

During pregnancy women or mother animals as well as can be immunized against bacterial pathogens. For the isolation of immunoglobulins from immunized donors the isolation of antibodies from milk or colostral milk from immunized cows or from eggs from immunized hens is prefered.

For the immunization preferably bacteria from the group of *Campylobacter jejuni, Helicobacter pylori,* Human pathogenic Yersinia and from Borrelia are used. Especially prefered is the immunization with a mixture of bacteria or the corresponding mixture of antigens from *Campylobacter jejunii, Helicobacter pylori, Yersinia enterocolitica* and/or pseudotuberculosis and from *Borrelia burgdorferi* sensu lato. A colostral milk from immunized mammals is for example described in EP-A 0 046 909. Procedures for immunization are therefore well known.

The antibodies against *Campylobacter jejuni, Helicobacter pylori,* yersinia or borrelia can also be produced as monoclonal antibodies in cell culture, isolated in known a manner and added to the immunoglobulin preparation or used alone.

Patients with chronic pain, especially those with antibodies against one or several bacteria from the group of *Campylobacter jejuni, Helicobacter pylori,* Yersinia and Borrelia in their plasma but without having signs of an acute or chronic infection or illness were treated with a dosage of 1 to 20 g, a prefered dosage of 1 to 10 g and especially prefered with 10 g immunoglobulin per day per os.

The immunoglobulins for oral therapy of chronic pain are produced according to in itself known procedures, as published e.g. in EP 0 413 187, EP 0 338 229 and EP 0 471 890. EP-A 0 413 187 describes a method for the production of immunoglobulin preparations by fractionation of a human blood protein fraction containing immunoglobulins of the IgG, IgA and IgM class in concentrated form. This preparation is highly purified because it is intended for intravenous administraion in humans.

The EP-A 0 471 890 reveals a method for the preparation of sterile filtered colostral milk, where the colostral milk can also be taken from immunized mammals.

The EP-A 0338 229 refers to a method for the preparation with antibody activity from colostral milk from non immunized mammals. In fact an intravenous and an oral administration of the product was suggested, but no differences in effectiveness were described but only the good tolerability of the product.

A method for the production of immunoglobulins from eggs especially from hen eggs is described in EP 0 225 254. Also in this connection the animals can be immunized.

The preparation of monoclonal antibodies is also well known. A method for the isolation of highly purified monoclonal antibodies is published for example in EP-A 0 530 447.

These preparations contain antibodies having activity against antigens from *Campylobacter jejunii, Helicobacter Pylori,* Human pathogenic *Yersinia sp.* and/or Borrelia. It is at present still unknown in which way these antibody activities or eventually other activities of these preparations in the gut affect the development or maintanance of chronic pain. Perhaps there is a certain cross reactivity of antibacterial antibodies against neuronal structures in chronic pain patients. After a bacterial infection has been cured the antibodies may persist and can cause severe pain in an unknown manner. In no case has a known infection been the cause of this kind of pain. Beyond that, the effectiveness of the oral therapy acording to the invention must be different from the effectiveness of intravenously administered immunoglobulins, because the antibody molecules can not translocate in an intact, native form from the gut into the blood, but are proteolytically degraded in the gut lumen or they are excreted with the fecec. These differences are also observable in the strength of the effectiveness and it's durability.

The prefered dosage for the oral administration of the immunoglobulin preparations is 1 to 20 g per day and especially prefered 10 g per day. If necessary it may be advantageous to combine the oral and intravenous administration of the immunoglobulin preparations, where the prefered dosage for oral administration is 1 to 10 g per day and especially prefered 10 g per day and the prefered dosage for the intravenous administration is 5 to 10 g per day and especially prefered 10 g per day. For the intravenous application the immunoglobulins must be of human origin. The treatment period for the oral administration can be some days up to some weeks. The additional therapy with intravenous immunoglobulins if necessary is lasting 2 to 5 days in such a treatment period.

Beyond that it has been turned out to use means for the the reduction resp. the partial or complete neutralization of gastric acid before or at the same time of the administration of the immunoglobulin preparation. Among such means are proton pump inhibitors like e.g. omeprazol and H2-blocking agents like e.g. ranitidin.

Taken together about 50% of the patients with chronic pain and positive findings of antibodies against bacterial pathogens respond to this therapy. In principle also indicated is the prophylactic oral administration of immunoglobulins to patients who had recovered from bacterial infections a long time ago and are for the present free of symptoms, but who should be treated prophylactically acording to the invention.

In the following the effectiveness of the use of oral administered immunoglobulins according to the invention will be demonstrated with some exemplary cases of patients suffering from severe chronic pain.

EXAMPLE 1

A 25 year old woman had extreme pain in her jaw and a facial swelling after dental treatment. At first antibiotics and antiphlogistics could soothe the pain. In the following time a long lasting treatment with opiats were neccessary with subsequent strong development of tolerance, increasing nausea and massive obstipation. The intravenous administration of human immunoglobulin (IgG) caused a further intensification of the pain with subsequent short time relief. The repetition of the intravenous administration of IgG was followed by severe intensification of the pain and decreasing subsequent pain relief.

The oral administration of 1,8 g polyvalent IgG-immunoglobulin (Sandoglobulin) per day for one week together with simultaneous blockade of the secretion of gastric acid in the gut by omeprazol prior to each IgG intake led to an increasing soothing of the pain without the intermediate intensification of the pain up to total freedom of pain. Already two days after treatment the opiate dosage could be discontinued slowly. Afterwards the patient was six weeks free from pain. Subsequent minor relapses of the facial pain could be treated successfully with new therapy series with oral IgG-immunoglobulin.

Since then the patient was able to continue fully working.

EXAMPLE 2

A female patient with fibromyalgia syndrome, that means pain in the whole locomotor system as well as strongest onesided pain in the neck with motoric dysphagia was since 15 years continously under medical treatment, including also hospitalization in a psychosomatic clinic. She has a positive Borrelia and *Campylobacter jejuni* serology. A high dosage antibiosis given in four consecutive series resulted only in a relief of the pain for a short period of time. The patient showed an increasing pharmacodynamic resistance to opiates and as a consequence she tried to attemt suicide. Finally she was treated monthly with 9 bottles of polamidon (50 mg each). For four weeks the patient received orally 10 g per day of an immunoglobulin preparation from colostral milk, prepared by delipidation of the colostral milk, caseinprecipitation, removal of casein and concentration of the colostral whey with subsequent lyophilization. With the immunoblot technique antibodies against *Campylobacter jejuni* and *Yersinia enterocolitica* were detectable in a dilution of 1:6400 of the immunoglobulin solution with 5 g/100 ml immunoglobulin. By immunoblot antibodies against *Borrelia burgdorferi* sensu lato were detectable in a dilution of 1:200.

The patient's condition of pain improved dramatically. In the course of 14 days the opiates could be discontinued completely. The depressionen disappeared as well as the sleep disturbances. The patient is again able to work. After six month symptoms of the disease appeared again, which again disappeared under the repeated administration of the colostral milk preparation.

EXAMPLE 3

A 26 year old female patient suffered since 9 years from pain in varying parts of the axial skeleton reaching from the servical to the lumbosacral area, and had finally severest pain in the neck, shoulder and arm region with burning pain in both hands and forearms and she suffered from a bilateral epicondylitis humeri radialis. She had a strong feeling of illness and depressive psychosis. In the serum antibodies against *campylobacter jejuni* were detectable. They belonged to the IgG class. IgA antibodies were not detectable. This pointed to an overcome *Campylobacter jejuni* infection.

The patient received oral for six weeks every day 10 g of the preparation from example 2. After 10 days the depression disappeared and by short consequences all the other symptoms receded. 2 months after the end of the therapy again the pain in her arms reappeared. She was again treated with the colostral milk preparation for 14 days, whereby after a few days all symptoms disappeared again. The working ability was maintained.

EXAMPLE 4

A 20 year old female patient with recurrent pain in the knee-joints and both elbows (epicondylitis) suffered under severe pain attacks with simultaneous appearing depressions. In the serum antibodies against *Yersinia enterocolitica* were detectable in her serum. There was no indication of diseases of the rheumatic syndrome in the sense of a reactive rheumatic arthritis caused by yersinia.

The patient received five weeks 10 g per day of the oral colostral milk preparation from example 2. The pain relief started very quick and already after two days the depressions disappeared. After one week the patient had only minor pain and was again able to work. After the discontinuation of the colostral immunoglobulin preparation the complete freedom of symptoms continued.

EXAMPLE 5

A 76 year old female patient suffered since 11 years under trigeminal neuralgia. 6 years ago medicinal therapy with carbamacepin failed for the first time. A remission of the neuralgia could only be achieved by a treatment with intravenous IgG. But again a relapse occured. In the meantime in the serum antibodies against Borrelia and *Yersinia enterocolitica* could be detected. A treatment with antibiotics and subsequent repeated treatment with intravenous IgG resulted in a relief of pain, so surgery was no longer necessary. Yet the patient had problems with the daily food intake because of heavy pain in the masticatory muscles (simultaneous pain symptom in the sense of myofascial facial pain).

Already 4 days after starting the therapy with an oral immunoglobulin preparation from colostral milk as described in example 2 she was free of symptoms. Omitting of treatment on trial after three and after five weeks let in each case to pain again both because of the neuralgia and the myofascial facial pain. After altogether 60 days of oral immunoglobulin therapy there has been finally complete remission even after the discontinuation of therapy.

EXAMPLE 6

A 46 year old female patient suffered after extraction of a wisdom tooth for six years under atypical facial pain. Because of suspected damage of the mandibular principal nerve in a new operation the damaged part of the nerve was replaced with a transplant of a nerve from the lower leg. After that a sudeck syndrome of the lower leg and the foot at the site of the donor aera of the nerve and complete incontinence of urine occured. The patient suffered since then under extreme pain in both parts of the body which finally led to incapacity to work. Even the treatment with morphine high dosage showed no sufficient effect. In the patient's serum antibodies against *campylobacter jejuni* could be detected.

A five time antibiotic treatment only had short time and clearly weakening effects. A therapy mit intravenous human immunoglobulin G resulted in an extreme intensification of the pain, which also were persisting for 3 weeks at a repetition of therapy. After that she had a short time improvement of pain for one week. The intensification of pain was accepted, because the administration of i.v. immunoglobulin eliminated incontinence of urine during the whole therapeutic period. The orale administration of an immunoglobulin preparation like described in example 2 resulted in a soothing of pain. An optimal soothing of pain was achieved in this patient with a combined administration of oral bovine immunoglobulins and the intravenous human immunoglobulin preparation. The oral administration of immunoglobulin prevented the earlier observed extreme intensification of the pain at the therapy with i.v. immunoglobulins. The morphine treatment could be reduced drastically and the patient is for the first time since 6 years again partly able to work.

We claim:

1. A method for treating myofascial pain, fibromyalgia or neuropathic pain without typical pathological and anatomical correlates in patients comprising administering a therapeutically effective amount of an oral immunoglobulin G to said patients.

2. The method according to claim 1 wherein said immunoglobulins have antibody activity against human pathogenic yersinia species.

3. The method according to claim 1, wherein the immunoglobulins have antibody activity against *Yersinia enterocolitica* or *Yersinia pseudotuberculosis*.

4. The method according to claim 1, wherein the immunoglobulins have antibody activity against *Campylobacter jejuni*.

5. The method according to claim 1, wherein the immunoglobulins have antibody activity against *Borrelia burgdorferi* sensu lato species.

6. The method according to claim 1, wherein before or during the administration of the immunoglobulins production of gastric acid in the stomach is reduced or neutralized.

7. The method according to claim 1, wherein omeprazol is used for the reduction of gastric acid in the stomach.

8. The method according to claim 1, further comprising the intravenous administration of an immunoglobulin.

9. The method according to claim 1, wherein said immunoglobulin is derived from immunized bovine colostral milk and hen eggs.

10. The method according to claim 1, wherein said immunoglobulin is derived from non-immunized bovine colostral milk and hen eggs.

* * * * *

UNITED STATES PATENT AND TRADEMARK OFFICE
CERTIFICATE OF CORRECTION

PATENT NO. : 5,871,731
DATED : February 16, 1999
INVENTOR(S) : Sprotte, et al.

It is certified that error appears in the above-identified patent and that said Letters Patent is hereby corrected as shown below:

Item [54]
Title Page & Col. 1 line 2    After " IMMUNOGLOBULIN " insert -- G --

Signed and Sealed this

Thirtieth Day of November, 1999

Attest:

Attesting Officer

Q. TODD DICKINSON

Acting Commissioner of Patents and Trademarks